US 7,641,343 B1

(12) United States Patent
Motamedi et al.

(10) Patent No.: US 7,641,343 B1
(45) Date of Patent: Jan. 5, 2010

(54) METHOD AND APPARATUS FOR EARLY DIAGNOSIS OF ALZHEIMER'S USING NON-INVASIVE EYE TOMOGRAPHY BY TERAHERTZ

(76) Inventors: Manouchehr E. Motamedi, 756 Paso De Leon, Newbury Park, CA (US) 91320; Ali Dabiri, 2290 MIddleton Way, San Diego, CA (US) 92109

( * ) Notice: Subject to any disclaimer, the term of this patent is extended or adjusted under 35 U.S.C. 154(b) by 291 days.

(21) Appl. No.: 11/880,911

(22) Filed: Jul. 26, 2007

(51) Int. Cl.
*A61B 3/10* (2006.01)
(52) U.S. Cl. .................. 351/221; 351/205; 359/245
(58) Field of Classification Search ........... 351/205, 351/220, 221
See application file for complete search history.

(56) References Cited

U.S. PATENT DOCUMENTS

| | | | |
|---|---|---|---|
| 4,170,987 A | 10/1979 | Anselmo et al. | |
| 4,515,165 A | 5/1985 | Carrol | |
| 4,556,057 A | 12/1985 | Hiruma et al. | |
| 4,948,974 A | 8/1990 | Nelson et al. | |
| 5,172,685 A | 12/1992 | Nudelman | |
| 5,318,024 A | 6/1994 | Kittrell et al. | |
| 5,507,287 A | 4/1996 | Palcic et al. | |
| 5,782,770 A | 7/1998 | Mooradian et al. | |
| 6,078,047 A | 6/2000 | Mittleman et al. | |
| 6,162,186 A | 12/2000 | Scinto et al. | |
| 6,839,172 B1 | 1/2005 | Motamedi et al. | |
| 6,988,995 B2 | 1/2006 | Zhou et al. | |
| 6,992,824 B1 | 1/2006 | Motamedi et al. | |
| 7,335,883 B2 * | 2/2008 | Wallace et al. | 250/330 |
| 2003/0149346 A1 * | 8/2003 | Arnone et al. | 600/309 |
| 2007/0235650 A1 * | 10/2007 | Federici et al. | 250/341.8 |
| 2007/0296957 A1 * | 12/2007 | Fitzgerald et al. | 356/51 |

OTHER PUBLICATIONS

M.E. Motamedi, et al, "MOEM Scan Engine for Barcode Reading and Factory Automation," SPIE Proceeding of Miniaturized Systems with Microoptics and Micromechanics III, vol. 3276, pp. 66-80 San Jose, 1998.

\* cited by examiner

*Primary Examiner*—Jordan M. Schwartz (57) ABSTRACT

The objective of the present method and apparatus is to provide a portable diagnosis system for a quick and reliable method to examine the conditions of a human eye-lens. The method provides precise and safe technique for the early diagnosis of Alzheimer's Disease (AD) which is not involved brain surgery or biopsy. The detection of deposited layers of amyloid plaque in the eyes of the patient has been discovered to be a possible diagnosis solution. The disclosed method uses terahertz waves instead of laser for scanning the eye of the AD patient to precisely image the amyloid layer non-evasively in real time and to map the deposited plaque with high resolution which can easily distinguish the abnormality of an AD patient with the comparison of the patient eye-lens test to the available signature of a normal person and the signature of a person with common age-related cataracts.

4 Claims, 7 Drawing Sheets

Lens Characteristics:
D = 9 mm, T = 4 mm
n 1.38-1.4 (Focusing)

D=diameter, T=thichness, n=index of reflection

Focused on RNFL

METHOD AND APPARATUS FOR EARLY DIAGNOSIS OF ALZHEIMER'S USING NON-INVASIVE EYE TOMOGRAPHY BY TERAHERTZ

FIELD OF THE DISCLOSED METHOD AND APPARATUS

This method and apparatus is related to non-invasively detecting early development of Alzheimer by scanning patient eye and, in particular, relates to a method and apparatus for diagnosis and tomography using Terahertz imaging.

BACKGROUND OF PRIOR ARTS

Alzheimer's disease (AD) in a medical term is classified as a form of dementia, a group of conditions that gradually destroy brain cells. Alzheimer's generally appears in older persons, continuing steadily to disorder brain and gradually destroys a person's memory and ability to make judgments, communicate and carry out daily activities. Scientists now believe that the cause of AD is most likely due to the concentration of Beta-amyloid deposited in some part of the brain. As Alzheimer's progresses, patients may also experience changes in behavior during their personal lives, such as anger, agitation and sometimes even delusions or hallucinations.

There is not a cure and/or successful treatment for Alzheimer's. All the reported treatment methods do not show a light at the end of the tunnel. The results of the reported treatments are mostly either based on exercise, body treatment, or based on some herbal remedies and dietary supplements. One promising treatment reported by scientists at the University of South Florida promoting the most potent antioxidant EGCG (epigallocatechin-3-gallate), which is found in green tea. Scientists discovered if they treated the Alzheimer's patients with concentrated EGCG, it will reduce noticeable amount of their Beta-amyloid deposited in brain.

During the past few years, several breakthroughs for AD have been reported where all these breakthroughs are only effective on the early stages of Alzheimer's. Researchers from Rush University Medical Center in Chicago are working in gene transfer using very thin needles; inject the drug into the area of brain that deteriorates very early on Alzheimer's. This techniques and other similar methods are only promising if Alzheimer's has been detected at its early development.

If the patient is treated at the early stage of disease, the patient can have a relatively good life style even though he/she is not totally cured. Therefore, the diagnosis and early detection of Alzheimer's is highly desirable and it is in the world's interest. Many methods and suggestions are reported during the past decade in literatures and patent disclosures for Alzheimer's detection and diagnosis. Presently, there are no simple methods like blood or urine test that can detect Alzheimer's.

In the following there are several prior art methods presently used for early detection of Alzheimer's:

1. Testing the patient's memory by asking questions and studying the patient's family history to determine if Alzheimer's is present. This is not very reliable technique and it mostly is done by a family doctor as initial warning for Alzheimer's.
2. Brain scanning by such techniques as CT (computed tomography) and MRI (magnetic resonance imaging) could be used for AD diagnosis. The problem of these techniques is that they are only effective at the late stages of Alzheimer's which the damage is already done.
3. Researchers at New York University Medical Center have reported EEG (electroencephalogram) testing that measures electrical activity in the brain to pinpoint the early signs of Alzheimer's as warning signal. In this method, the measured brain activity of patient is compared to a standard activity of a patient with no Alzheimer's disease. This method still is at initial study stage and according to the scientists at Alzheimer's Association, there is concern that EGG study is too limited and the findings are too preliminary.
4. Researchers in the Netherlands reported that they can predict the early detection of Alzheimer's by measuring the size of two parts of the brain, the hippocampus, and amygdala. For those patients who have smaller sizes of these two parts against some standard have several time more likely to suffer from the Alzheimer's decease. The technique is still at study stage and mostly is looking for any type of dementia; they are not focusing on Alzheimer's. Another drawback of this technique is direct scanning of the brain which is likely harmful to patient.
5. There is a new technique recently reported by several institutes including Hazard Medical School and Brigham and Women's Hospital in Boston. The technique is detecting early phases of Alzheimer's disease by measuring the level of Beta-amyloid protein plaques deposited in the lens of the patient's eye using a non-invasive laser scanning and imaging. This new discovery could revolutionize early detections of Alzheimer's disease including most of the dementia disorders. All the previous measuring techniques have to use part of the brain for detection which is not advisable. The fact that the plaque (abnormal beta-amyloid protein) which deposits in the brain of Alzheimer's patient also will deposit simultaneously in the lens of the patient's eye similar to formation of cataracts, opens a new avenue for early diagnosis and continuous monitoring of Alzheimer's.

Among the above listed prior arts for early detection of Alzheimer's, the most promising technique is the last method, Alzheimer's diagnosis by laser scanning the lens of patient's eye. Laser imaging of the eye for AD detection has now been accepted among the researchers to be a promising technique.

One example is Sianto et al in U.S. Pat. No. 6,162,186 who is claiming that AD Patients' autonomic nervous system is hypersensitive to the neural transmitter mediators (NTM), used as eye drops, with concentration so low that did not affect the pupil's diameter change and other pupil's characteristics if applied on a person with no sign of being AD symptom. They use standard CCD camera to measure the change in a diameter and constriction of the pupil in the eye of an AD patient in a short time. For measuring the pupil's constriction velocity, the test is done under a low light with controlled intensity and duration. The inventors compare this data of an AD patient with some predefined standard data taken from normal persons.

Another example is Zhou et al, in U.S. Pat. No. 6,988,995 who is using a diode laser with 780 nm radiation. The laser light is first collimated and then scans in 2 dimensions by a resonance scanner and a galvanometer scanner. The scanned beam is taking data from the eye RNFL (retinal nerve fiber layers) compared with some standard signatures. The inventors claim that their method is using birefringence data of the structural elements of the eye with sufficient accuracy which is required to identify the effects of AD in the RNFL. The drawback of the invention is that there is no experimental data to support the invention. In this patent the laser power is not known and its safety is questionable. Even the inventors are not sure that the method is practical and there is no proof that the RNFL is affected by AD.

The present arts have at least three major drawbacks. The first one is high intensity laser scanning which is harmful to the patient's eyes and sometimes extremely dangerous if it has to penetrate inside the layers of the deposited plague. The second problem of the existing disclosed methods is the requirement of large, heavy, and expensive apparatus which makes testing inconvenient to be done in Doctors' office and the patient has to go to hospital. The third drawback is the lack of a very sensitive and highly efficient testing process which is required for early detection of the AD symptoms.

From the above discussions of the prior arts, the only presently known means of positively proving and demonstration of AD case in a person can only be achieved by a brain biopsy or a postmortem examination to determine existing of the plaque (amyloid) in brain tissue. It is overwhelmingly obvious that there has been remained a large demand for an accurate diagnosis for these AD symptoms which do not include brain biopsy, surgery, or even using the harmful high dose MRI and CT.

BRIEF SUMMARY OF THE DISCLOSED METHOD AND APPARATUS

The primary objective of the present method and apparatus is to provide new systems and technique for the early diagnosis of Alzheimer's Disease which is not involved brain surgery or biopsy. Based on the above background of the prior arts, it is clear that a precise and accurate measurement of the Alzheimer's deposited layers of amyloid (plaque) in the eyes of the patient is a possible solution.

The disclosed method and apparatus use terahertz waves instead of laser for scanning the eye of the AD patient to precisely image the amyloid layer non-invasively in real time to determine the deposited plaque of amyloid with very high resolution by dividing the amyloid layer thickness to a large number of very thin microlayers. Each microlayer independently is scanned by terahertz waves and all microlayers' images are integrated to generate a well defined signature of the AD patient eyes. The accuracy and high resolution of this method can easily distinguish the abnormality of an AD patient with the signature of a normal person and the signature of a person with common age-related cataracts.

Terahertz waves are a segment of electromagnetic waves. Terahertz waves are bounded between millimeters waves (less than $1 \times 10^{11}$ Hz) and photonics waves (greater than $1 \times 10^{13}$ Hz). The electromagnetic frequencies lower than terahertz band are covering mm waves (microwaves), while the electromagnetic frequencies higher than terahertz band are covering near infrared through visible spectrum.

Terahertz wave band can be used for time domain and frequency domain imaging. The present applications of terahertz waves are spectroscopy in atmospheric science and in astronomy, imaging for burn diagnostics, tomography, biomedical, medical diagnostics, screening for weapon, explosives, biohazard, imaging of concealed objects, and cancerous tissue detection.

Existing water in living tissue limits the penetration depth of terahertz energy to a few millimeters, which is just sufficient for the diagnosis of RNFL which has a thickness of less than 200 microns. Terahertz waves above 0.5 THz can travel in air up to a meter, which is more than sufficient to transmit and receive signals from an eye test.

Besides detecting the presence of AD, the present method and apparatus is also valuable to determine how advance is the concentration of Amyloid plaques as well as information regarding whether the progression has stopped or has slowed down. A map showing, the difference between AD plaques and age-related cataracts, can aid in the accurate diagnosis of AD with no ambiguity. This is in contrast to the poor resolution of the prior art using laser techniques. When using terahertz systems such as disclosed herein, the combination of the spatial resolution and the high spectral resolution of a terahertz imaging system can be utilized to detect Alzheimer's progression with high level of confidence.

The present method and apparatus gathers data in three spatial dimensions. Initially, a spot is selected on the outer ring of the lens of the eye which is the location of the AD plaques deposition. The spot travels in depth where a line image is constructed resulting from a rapid optical delay line, so called optical coherence topography (OCT). The depth of the RNFL is binned according to the desired spatial resolution, signal-to-noise ratio, and the characteristic of the rapid optical delay line. Then, the incident beam will be scanned in two directions collecting three dimensional data of a rectangular area alongside of the deposited ring. To improve the reliability of this method several rectangular areas of the outer ring of the patient's eye are selected for similar experiment. A tomography will then be constructed from the gathered overall data.

A better understanding could be achieved with reference to Detailed Description of the disclosed method and apparatus and with reference to the drawings. The description represents a particular case to realize the disclosed method and apparatus and is not intended to define the invention, but merely to provide adequate support for the claims appended hereto. Accordingly, the invention is defined solely by the claims to the invention appended hereto.

DETAILED DESCRIPTION

Figure 1:
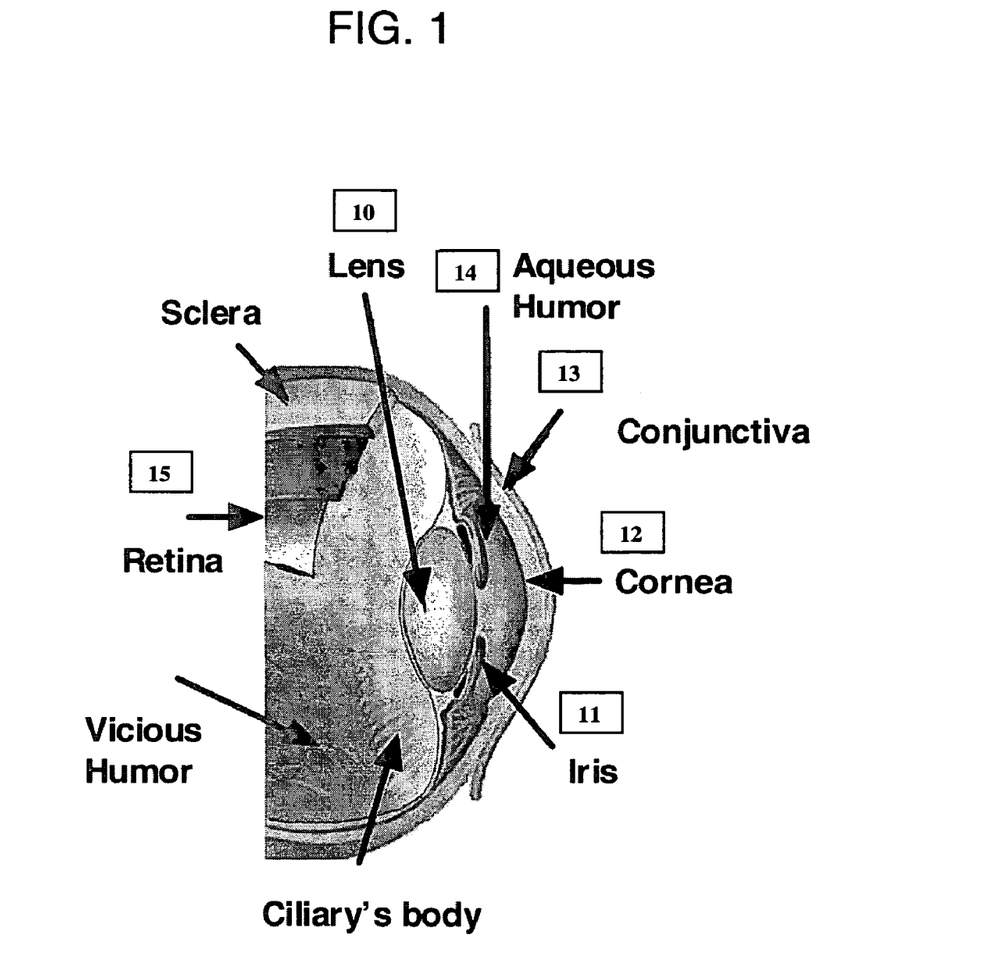
FIG. 1 is a diagram of the human eye showing its main structures.

FIG. 1 is a diagram of the human eye's structure which shows the lens 10 dimension relative to other elements of the eye. The lens focuses light rays onto the retina. An iris 11, the color part of the eye changes the amount of the light requires for optical processing. The eye acts as a perfect high resolution camera. It uses its variable index of reflection to dynamically focus a subject. Cornea 12 is bounded between conjunctiva 13 and aqueous Humor 14. Retina 15 works as an image processor to convert incoming rays into nerves signals where the brain analyzes the signals and creates the image.

Figure 2:
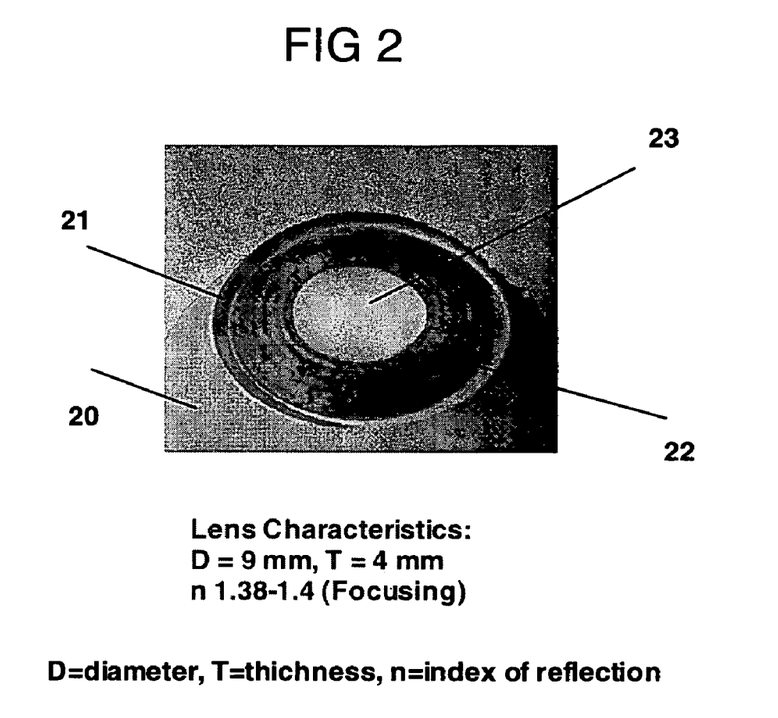
FIG. 2 is characterization and data in the lens of Human's eye
Figure 3:
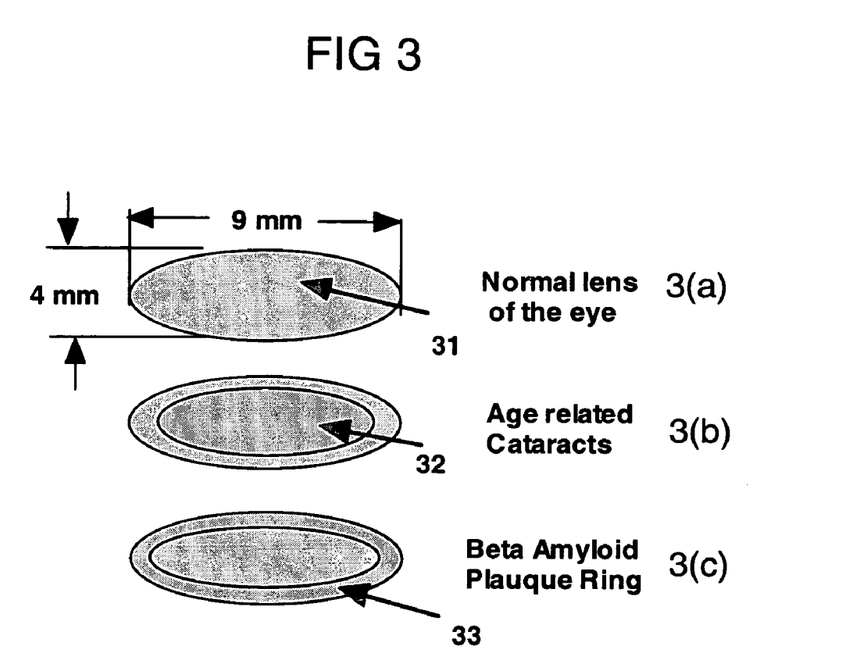
FIG. 3 is Alzheimer's signature compared with age related cataracts

FIG. 2 is a close up picture of the eye 20 where the lens 21 is partially exposed by iris 22 acts as a diaphragm and partially exposed the lens in the opening pupil 23. The lens normal characteristics have shown in FIG. 2. FIG. 3 shows a comparison between Alzheimer's plaques deposited in the lens of the patient's eye and the cataracts plaques deposited similarly in the lens of the eye in age related cataracts symptom. The lens of the eye 31 has a dimension of 9 mm in length and 4 mm in thickness. The thickness of the plaques deposited is normally about 200 microns and most likely the plaque is deposited in different locations. FIG. 3(a) shows the lens coloration 31 of an ordinary person. The age related cataracts patient, see FIG. 3(b), where the plaques 32 is deposited in the center of the lens while the Alzheimer's patient with the Beta amyloid plaques 33 have the same dark coloration, see FIG. 3(c), but is deposited as a ring in the outward portion of the lens.

Figure 4:
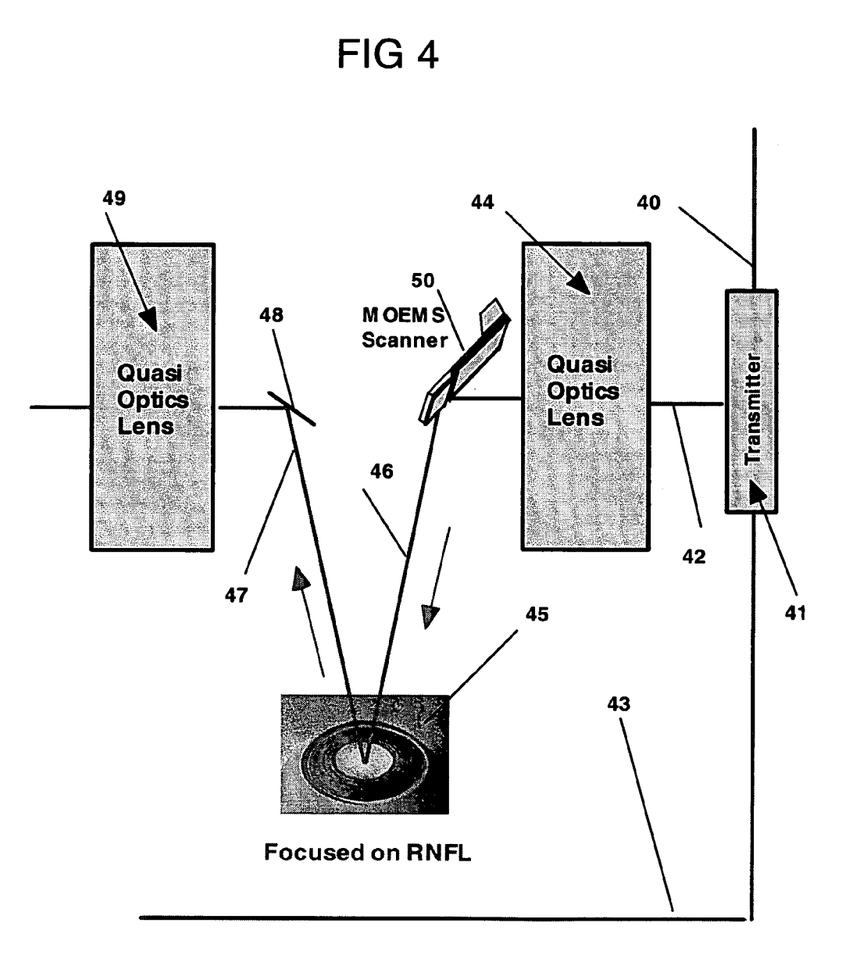
FIG. 4 is a simplified diagram of the THz scanning the lens of Patient's eye

The FIG. 4 is a simplified diagram of the AD detection by scanning the lens of the patient's eye using the Terahertz wave imaging. A beam of the femtosecond pulsed laser 40 enters the Terahertz transmitter 41 electronically controlled by the line 43. The output of the transmitter 42 is using high efficient quasi optics lenses to focus the THz beam on the mirror surface of a MOEMS scanner 50. The scanned THz waves 46 are programmed to scan the surface of the lens 45. The reflection 47 from the lens of the patient eye is collected by the mirror 48 and is focused by quasi optics lens 49 onto a detector shown in detailed block diagram of the invention in FIG. 5. The detector preferably has the same structure and principles as discussed for the transmitter system 41. The received signal at the detector has an inherently high signal to noise ratio. The detection process works based on convolution of two electromagnetic waves coming in opposite direction and mixed (see the detail in FIG. 5). As THz beam is penetrated inside the lens of the eye about at least 2 mm, more than 10 layers can be image and processed. Since the thickness of the AD plaques is only about 200 microns, the first 10 layers, give the signature of the Alzheimer's disease.

Figure 5:
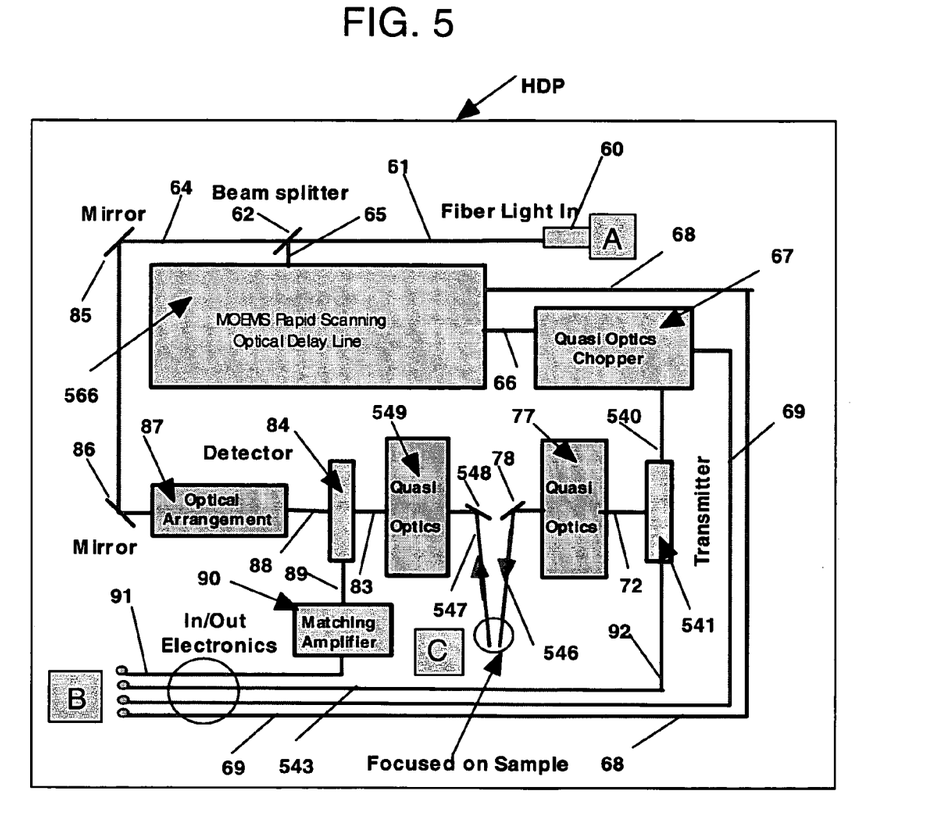
FIG. 5 is a detailed block diagram of the diagnostic of the present invention.
Figure 6:
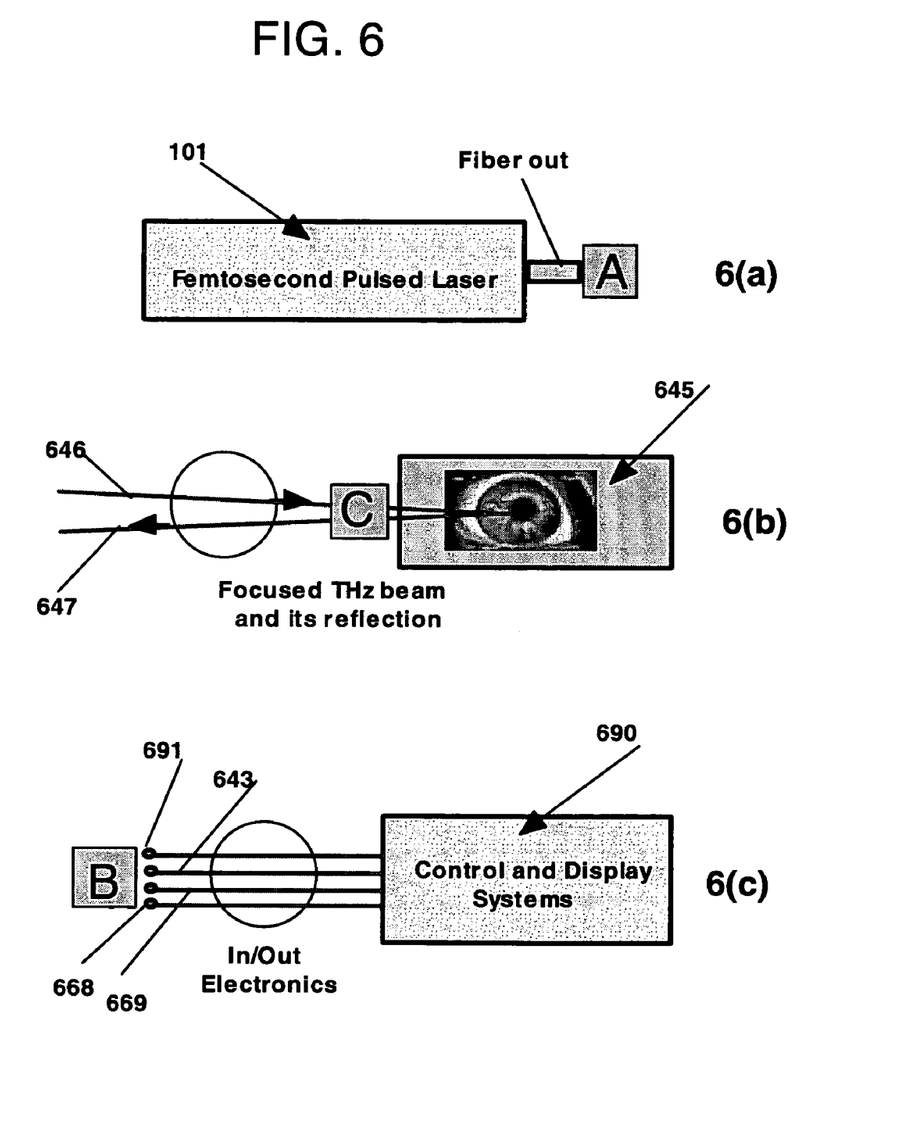
FIG. 6 is detailed of the FIG. 5 in three locations of A, B, and C.

As shown in FIG. 5, a fiber carrier laser light 60, in accordance with the present method and apparatus is generated by a femtosecond pulsed laser 101 shown in FIG. 6 with wavelength typically between 800 nanometers to 1.5 µm. The laser light is gated by time domain pulses, the durations of which are preferably measured in femtoseconds. The frequency spectrum of a femtosecond pulse is rather wide, covering from 300 GHz to 10 THz (10,000 GHz). The output beam of the pulsed laser 101 is coupled to the fiber carrier laser light 60 shown in FIG. 5, thus transferring the femtosecond pulses to a handheld diagnostic probe (HDP) sketched in FIG. 5. All components contained in HDP are shown in FIG. 5. All components required for HDP operation that lie outside the HDP are shown in FIG. 6. The laser light 61 inside the HDP will split into a pump light 65 and a reference (probe) light 64 by a beam splitter 62.

Figure 7:
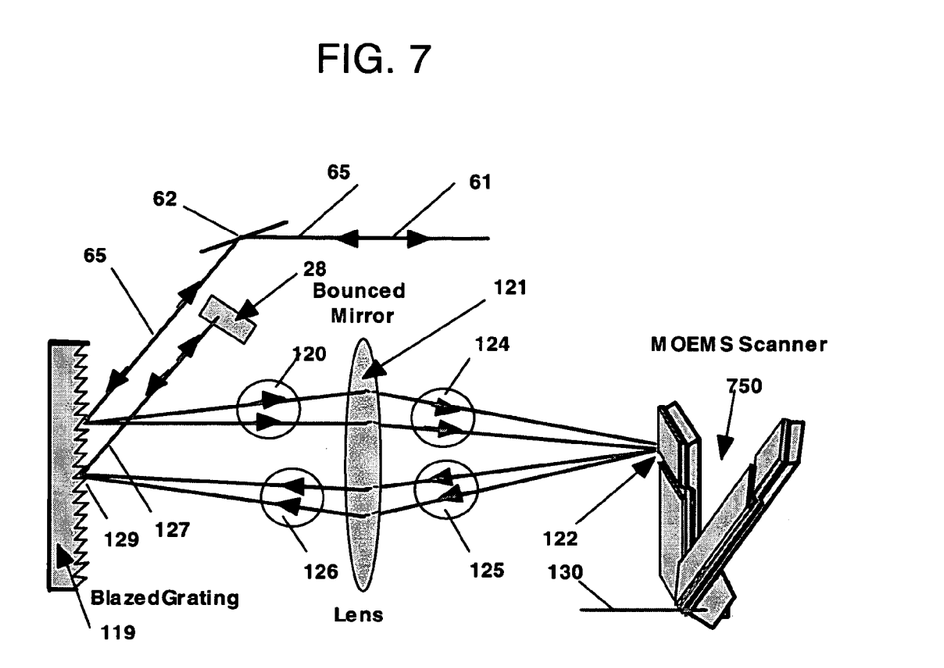
FIG. 7 is a block diagram of the MOEMS rapid scanning optical delay line.

The pump light 65 will enter a micro-opto-electro-mechanical systems (MOEMS) rapid scanning optical delay line (RSOD) 566. The detail description of the MOEMS RSOD 566 is provided in Motamedi, et al, U.S. Pat. No. 6,839,172 entitled "Enhanced sampling rate in time domain imaging using MOEMS scanning optical delay line" and its components are shown in FIG. 7. As shown in FIG. 7, pump beam 65 will reflect by mirror 62 to a special design blazed grating 119. Beam 65 will split in zero and +1 diffraction order beams 120. The beams 120 focuses through a lens 121 on a MOEMS scanner mirror 122. MOEMS scanner 750 has potential to have large-size mirrors (more than 10 mm²) and a surface flatness on the order of optical wavelength, as described in an article entitled "MOEM Scan Engine for Barcode Reading and Factory Automation" by M. E. Motamedi, et al published in SPIE Proceeding of Miniaturized Systems with Micro-optics and Micromechanics III, Vol., 3276, p. p. 66-80, 1998.

The reflection beam 125 from scanner mirror 122 is setup to pass through the same lens 121 and refocuses again to beams 126 arriving at a new location on grating 119, combining to a single beam. A bouncing mirror is mounted in proper location which returns the light beam 127 back through lens 121 and scanner mirror 122 and redirects the beam back from the path beam 65 and mirror 62 to the direction of beam 61 where was originated. As the scanner mirror 122 relocates to a new location, the return beams 126 will move on the surface of the grating 119 from location 129 to another grating location generating time delays of tens of picoseconds. The power required for operating the MOEMS RSOD is fed through the HDP connector 668 from control and display system 690 shown in FIG. 6.

The return scanning delayed beam is output through beam light 66 from the RSOD line to a quasi-optics chopper 67. The input power and the returned chopping signals are coupled from the quasi optics chopper 67 to the control and display system 690 through connector 69. The chopped beam output 540 exits from the quasi optics chopper system 67 and enters a terahertz transmitter system 541. The transmitter system 541 is a preferably a solid state, semi-insulated GaAs, electromagnetic emitter coupled by metal-film strip lines about 10 µm wide and spaced 100 µm apart. For the purpose of this description, the transmission lines are considered to be part of the transmitter system 541. As the number of the lines increases, the emitter bandwidth decreases. If the transmitter is excited by a train of femtosecond pulses emitted from the beam quasi optics chopper 67, the strip lines in the transmitter system 541 act as an antenna and radiate waves in the terahertz spectrum. If only two strips are used, the system 541 radiates in a spectrum ranging from 100 GHz to sometimes 10 THz. In the presently disclosed method and apparatus, the particular range of terahertz frequencies will be selected in accordance with what is demanded by type of diagnostic or other application. The transmitter system 541 requires a DC voltage for biasing, which is provided through the connector 92 from the system 690 shown in FIG. 6.

The terahertz waves 72 emitted from the transmitter system 541 are focused through a quasi optics lens 77 and a mirror surface of a MOEMS scanner 78 to the eye sample 645 shown in FIG. 6. The eye sample 645, which is outside the probe, is diagnosed by a projection beam 646 (shown in both FIG. 5 and FIG. 6) and its reflection beam 647. The focusing spot and its propagation through the eye lens 10 of FIG. 1 and its detailed description 21 in FIG. 2, taking into consideration the diffusion and dispersion phenomenon are controlled by quasi optics lens 77 shown in FIG. 5. To cover a large area of eye lens 21 in FIG. 2, the patient's eye lens should stays stationary, and the beam should be scanned inside the probe by a MOEM scanner 50. This option is shown in FIG. 4.

The reflection 547 from patient's eye in FIG. 5 is collected by the mirror 548 and is focused by quasi optics lens 549 onto a detector 84. The detector 84 preferably has the same structure and principles as discussed for the transmitter system 541. The received signal at the detector 87 has an inherently high signal to noise ratio, but it suffers significantly from misalignment and large bandwidth requirements. The detection process works based on convolution of two electromagnetic waves coming in opposite direction and mixed. Since the mixed waves are identical in characteristic when split at beam splitter 62, the detector acts as a convolver where the difference signal has the frequency of scanner 50 shown in FIG. 4 with diagnosis information of the eye lens under test.

The probe beam 64, which is split from beam splitter 62, enters in optical arrangement 87 via mirrors 85 and 86. A controlled terahertz reference beam 88 exits from the optical arrangement 87 and enters the detector 84 at the exact time as the reflected terahertz signal 547 carrying information regarding the patient's eye test. The mixing of these two terahertz waves within the detector 84 will detect the eye testing information. The detected output has high input impedance. The output preferably goes through several improvement stages, including a matching impedance amplifier 90. Using a MOEMS high speed scanning delay line allows the layer information of the eye under test to be collected. In addition, a representative tomography of the Amyloid layer volume is constructed. The test information of the detector 84 is transferred in real time to the display and control system 690 shown in FIG. 6. The detector 84 is coupled to the display and control system 690 through the connector 91. The diagnosis results can then be displayed in a handheld display system. Alternatively, the diagnosis results could be transmitted to a medical center by means such as wireless communications.

The tissue image is comprised of a plurality of horizontal bands, each band being adjacent to another, with equal bandwidths and comprised of a plurality of pixels where each pixel being adjacent to another. The images with a calibrated reference are stored in a handheld memory, indicating regions of coincidence and region of non-coincidence, and combining the images at different layers to obtain the tomography of the eye Amyloid layer.

It should be understood by those skilled in the art that modifications from the disclosed method and apparatus may be made without departing from the spirit of the invention claimed in the appended claims provided herein. Furthermore, the invention is defined only by the appended claims. Accordingly, it will be understood that the above description is provided only to enable one of ordinary skill in the art to make and use the invention. However, departures from the disclosed method and apparatus that fall within the scope of the claims should be considered to be within the scope of the claimed invention.

We claim:

1. An apparatus for early diagnosis of Alzheimer, by an eye lens test, comprising:
   a) a light source;
   b) a MOEMS rapid scanning delay line coupled to the light source;
   c) a quasi optics chopper coupled to the MOEMS rapid scanning delay line;
   d) a terahertz transmitter coupled to the quasi optics chopper;
   e) a first quasi optics system coupled to the transmitter;
   f) a terahertz light output from the first quasi optics system scanned onto the mirror of a MOEMS scanner;
   g) a MOEMS scanner to scan the lens of the eye in two dimensions;
   h) a second quasi optics system optically coupled to the eye-lens under test, the second quasi optics system receiving light reflected from the eye-lens;
   i) a detector coupled to the second quasi optic system;
   j) a matching amplifier coupled to the detector and;
   k) a control and display system; and
   l) an optical arrangement system to feed a reference light from the light source and the reflected light from the eye lens to the detector for convolving collected data from the eye lens and improving the signal to noise ratio.

2. The apparatus of claim 1, wherein the light source is a femtosecond pulsed-laser and the light is transmitted through fiber for handheld diagnosis system.

3. The apparatus of claim 1, wherein the MOEMS scanner and display system are inside a handheld system together with the other elements recited in claim 1.

4. The apparatus of claim 1, wherein the first and the second quasi optics are kinoform lenses, suitable for size reduction for handheld diagnosis system.

\* \* \* \* \*